(12) United States Patent  
Batug et al.

(10) Patent No.: US 6,701,255 B2
(45) Date of Patent: Mar. 2, 2004

(54) EMISSION MONITORING SYSTEM AND METHOD

(75) Inventors: James P. Batug, Macungie, PA (US); Carlos E. Romero, Bethlehem, PA (US); Ali Yilmaz, Worcester, MA (US); Edward K. Levy, Bethlehem, PA (US); Noel Moyer, Allentown, PA (US)

(73) Assignee: PPL Electric Utilities Corp., Allentown, PA (US)

(*) Notice: Subject to any disclaimer, the term of this patent is extended or adjusted under 35 U.S.C. 154(b) by 0 days.

(21) Appl. No.: 09/844,282

(22) Filed: Apr. 30, 2001

(65) Prior Publication Data

US 2002/0059033 A1 May 16, 2002

Related U.S. Application Data

(60) Provisional application No. 60/200,502, filed on Apr. 28, 2000.

(51) Int. Cl.⁷ .......................... G01N 31/00; G06F 19/00
(52) U.S. Cl. .............. 702/24; 702/1; 700/31; 436/161; 422/62; 73/863.21; 73/116; 73/23.31; 250/338.5; 60/274
(58) Field of Search .......... 702/1, 24; 700/31; 436/161; 422/62; 250/338.5; 73/863.21, 116, 23.31; 60/274; 123/3

(56) References Cited

U.S. PATENT DOCUMENTS

| 4,094,187 | A |   | 6/1978 | Navarre, Jr. ............... 73/1 G |
| 4,586,367 | A | * | 5/1986 | Lewis ...................... 73/116 |
| 4,881,183 | A | * | 11/1989 | Groe ........................ 702/1 |
| 5,210,702 | A | * | 5/1993 | Bishop et al. ............ 250/338.5 |
| 5,423,228 | A | * | 6/1995 | Budd et al. .............. 73/863.21 |
| 5,524,432 | A | * | 6/1996 | Hansel ...................... 60/274 |
| 5,596,154 | A | * | 1/1997 | Baughman ................ 73/23.31 |
| 5,635,652 | A |   | 6/1997 | Beaudin .................. 73/863.03 |
| 5,668,735 | A | * | 9/1997 | Dominguez et al. ........ 436/161 |
| 5,729,452 | A | * | 3/1998 | Smith et al. ................. 700/31 |
| 5,846,831 | A | * | 12/1998 | Silvis ......................... 422/62 |
| 5,947,063 | A | * | 9/1999 | Smith et al. ................. 123/3 |
| 5,968,452 | A | * | 10/1999 | Silvis ......................... 422/62 |
| 6,094,968 | A | * | 8/2000 | Scheufler et al. ............ 702/77 |
| 6,482,649 | B1 | * | 11/2002 | Gogol et al. ................. 436/34 |

FOREIGN PATENT DOCUMENTS

| DE | 40 18 872 A1 | 12/1991 |
| DE | 195 23 599 A1 | 2/1997 |
| EP | 0 471 174 A2 | 2/1992 |

* cited by examiner

Primary Examiner—John Barlow
Assistant Examiner—Aditya Bhat
(74) Attorney, Agent, or Firm—Morgan, Lewis & Bockius LLP (57) ABSTRACT

An emission measuring system and method provide an accurate, real-time calculation of a particular material emitted from an emission source. Specifically, a CEM system installed in an industrial stack can include a dilution probe located in the stack and a data analyzer that records and analyzes characteristic data of the materials sampled by the dilution probe. A dilution ratio is used to correct for the addition of dilution gas into the stack gas sample to determine the concentration of a particular material that is being emitted from the stack. The dilution ratio is based on a molar flow rate, which can be determined by using specific algorithms and measurements.

22 Claims, 7 Drawing Sheets

EMISSION MONITORING SYSTEM AND METHOD

This application claims priority and benefit of U.S. Provisional Patent Application No. 60/200,502, filed on Apr. 28, 2000 and entitled Emission Monitoring System and Method, which is hereby incorporated by reference.

BACKGROUND OF THE INVENTION

1. Field of the Invention

The invention concerns a monitoring system and method for determining the amount of a material that is emitted from a particular source. More specifically, the invention is directed to a Continuous Emission Monitoring (CEM) system based on a sampling sub-system with a dilution-type extractive probe used in a fossil-fired power plant or in an industrial facility to determine the concentrations of gaseous species emitted from the stack or chimney of the facility. The invention also is directed to analyzer-based process monitoring systems based on a sampling sub-system with a dilution-type extractive probe to measure the concentration of gaseous species in process gases for the purpose of process monitoring, control, and quality assurance.

2. Discussion of the Related Art

The Environmental Protection Agency (EPA) requires power generating plants and other industrial facilities to report pollutant emissions and, based upon reported emissions, sets up a market-based trading system for establishing emissions allowances. Accordingly, it is advantageous for industries to record emissions from its plants as accurately as possible. Conventionally, a CEM system is used to analyze and correct data received from a probe located in or adjacent to a stack or ducts to determine the contents of gas that is emitted from the plant.

Industrial plants commonly use a CEM system with "dilution-type sampling." Such a CEM system uses a dilution probe, which is inserted into the plant's stack or ducts to obtain sample emissions of the flue gas. The sampled gas containing pollutant and/or other combustion by-products is typically referred to as flue gas, sample stack gas or emission gas and can also be considered emitted material. The dilution probe can be located anywhere in the ductwork, air pollution equipment or stack where a representative volume of flue gas can be obtained. The dilution probe of the CEM system includes an inlet for the sample gas, two input gas lines (dilution gas line and calibration gas line) and one output gas line (diluted sample gas line). In operation, a dilution gas, which can comprise clean dry dilution air, is injected into a venturi device causing flue gas to be drawn into the venturi through a sonic (critical) orifice. The flue gas is mixed with dilution air to create mixed dilution sample gas. The mixed dilution sample gas is then delivered to an analyzer via the diluted sample gas line, and the analyzer determines the concentration of emitted pollutants in the mixed diluted sample gas. A particulate filter is often included in the dilution probe to remove particulate matter from the sample gas upstream of the sonic orifice to prevent plugging.

In order to consistently measure the contents of stack emissions, a dilution ratio is determined and used to manipulate the data output by the analyzer. Specifically, the dilution ratio is multiplied by the results from the analyzer to compensate (or correct) for the effect of dilution air in the flue gas being analyzed. The result is an indication of the concentration of the different materials, e.g., pollutants, being emitted in the flue gas.

Typically, the dilution ratio has been defined by the following formula based on inferred volumetric measurements of dilution and flue gases:

$$D=(Q_{dil}+Q_{stack})/Q_{stack} \quad (1)$$

where D is the dilution ratio, $Q_{stack}$ is the volumetric flow of flue gas and $Q_{dil}$ is the volumetric flow of dilution air.

The data obtained from the analyzer are converted to determine the concentrations of various gaseous species being discharged from the stack. This is done by multiplying the analyzer readings by the dilution ratio evaluated at the time of calibration, as follows:

$$C_{sack}=C_{analyzer} \cdot D \quad (2)$$

However, several variables affect the calculation of the dilution ratio. These variables include the use of unheated dilution probes, temperature differential errors that occur when using a heated dilution probe, variability of stack and barometric pressure, inadequate dilution air pressure regulation, inadequate internal heat exchanger performance, variability of temperature in the sampling system transport lines or umbilical, variability of molecular weight of the calibration, reference, and flue gases, variability of calibration gas flow rate induced temperature effects on dilution air mass flow rate, variability of calibration gas flow rate induced pressure effects on sonic orifice inlet (stagnation) pressure, dilution probe temperature, sample temperature, and dilution air supply pressure. Thus, the dilution ratio typically used in CEM systems can be inaccurate and this results in errors in reported emissions or process data.

A CEM system must also be calibrated periodically to ensure accurate readings. In order to calibrate a CEM system dilution probe, calibration or reference gases are injected into the probe. The calibration verifies that the system errors at zero, low, mid and high concentration levels are within prescribed acceptable limits. These calibration or reference gases can also be referred to as span gases.

One example of an attempt to account for variations in the dilution ratio is disclosed in U.S. Pat. No. 5,596,154 to Baughman (the '154 patent). The '154 patent discloses a dilution control apparatus for use in a CEM system which includes a regulator for regulating the flow of dilution gas to a dilution probe, a mechanism for measuring changes in gas density of the emission gas and a mechanism for determining an adjusted flow rate of the dilution gas based on the measured changes in gas density to control the dilution ratio. The "gas density" measured by the device disclosed in the '154 patent is a measure of change in stack and atmospheric pressures (see column 4 lines 38–40 of the '154 patent specification). In operation, the device disclosed in the '154 patent monitors the stack and atmospheric pressures and, upon a change in "gas density", determines an adjusted flow rate of dilution gas and regulates the flow rate of dilution gas to the adjusted flow rate. Accordingly, the dilution ratio is maintained constant during the sampling process and less data manipulation is necessary to determine the constituents of the stack gas from the stored analyzer data.

Several problems exist in the conventional systems for correcting the dilution ratio such as disclosed in the '154 patent. Specifically, the calculation of the material emitted from the stack can be inaccurate due to the fluctuation of variables during sampling of the stack gas. These variables include dilution probe temperature, sample absolute pressure, sample temperature, dilution air supply pressure, calibration gas molecular weight, sample gas molecular weight, and umbilical cable temperatures. In addition, physical control of various stack emission and data gathering parameters can be expensive and difficult to operate and can further intensify the possibility of error in calculation of the material constituents of the stack emission.

SUMMARY OF THE INVENTION

In light of the above points, an object of the invention is to provide a CEM system and method that more accurately measures material and/or pollutants emitted from a source (e.g., a stack). The invention includes a CEM system that utilizes a dilution ratio based on molar flow rates of dilution air and flue gases in order to obtain a more accurate dilution ratio. The invention enables a more consistent and precise measurement of the concentrations of gaseous species emitted from a source without requiring additional mechanisms for controlling parameters of flue gas flow. The formula for dilution ratio based on molar flow rates is as follows:

$$D = (\dot{n}_{dil} + \dot{n}_{stack})/\dot{n}_{stack} \qquad (3)$$

where D is the dilution ratio, $\dot{n}_{dil}$ is the molar flow rate of dilution air, and $\dot{n}_{stack}$ is the molar flow rate of flue gas.

The molar flow rates of the gases are calculated using a functional equation (algorithm) based on various data measured at the stack, such as the temperature and pressure of the flue gas. Thus, not only does the dilution ratio (3) correct the data produced by the analyzer for error due to the presence of dilution air, but it also eliminates error due to different variables including pressures (dilution air supply pressure, barometric pressure, critical orifice stagnation pressure), temperatures (including dilution air supply temperature, stack or duct temperature, critical orifice stagnation temperature), calibration gas molecular weight, and sample molecular weight that affect the ratio between dilution air and flue gases. In addition, the invention improves gas measurement accuracy by reduction or elimination of uncertainty due to the following: use of unheated dilution probes; temperature differential errors that occur when using a heated dilution probe; variability of stack and barometric pressure; inadequate dilution air pressure regulation; inadequate internal heat exchanger performance; variability of temperature in the sampling system transport lines or umbilical; variability of molecular weight of the calibration, reference, and sample gases; variability of calibration gas flow rate induced temperature effects on dilution air mass flow rate; variability of calibration gas flow rate induced pressure effects on sonic orifice inlet (stagnation) pressure. Sampled gas molecular weight can also be corrected to constant test values or can be dynamically compensated if desired.

Additional features and advantages of the invention will be set forth in the description that follows, and in part, will be apparent from the description, or may be learned by practice of the invention. The objectives and other advantages of the invention will be realized and achieved by the structure particularly pointed out in the written description and claims hereof as well as the appended drawings.

To achieve this and other advantages, and in accordance with the purpose of the invention, as embodied and broadly described the present invention provides for a flow measurement and analysis device to be used in conjunction with a dilution probe. The combined system is capable of providing accurate measurement of the molar flow rate of sample gas and dilution air, which together flow to the gas analyzers for subsequent analysis of flue gas composition. In accordance with another aspect of the invention, a system for use with an emission source includes a data medium for receiving emissions data collected from sensors located at the emission source, the emissions data including an amount of a particular material emitted from the emission source, and means for calculating a total amount of the particular material emitted from the emission source using a mass flow rate value.

In accordance with yet another aspect of the invention, a method for calculating an amount of a material emitted from a source includes sensing an emission gas emitted from the source; determining a mass flow rate value of one of the emission gas and a dilution air; calculating a dilution ratio based on the determined mass flow rate value; and determining a characteristic of the emission gas using said dilution ratio.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Below, a preferred working configuration of the invention will be described in detail with reference to FIGS. 1 through 7.

Figure 1:
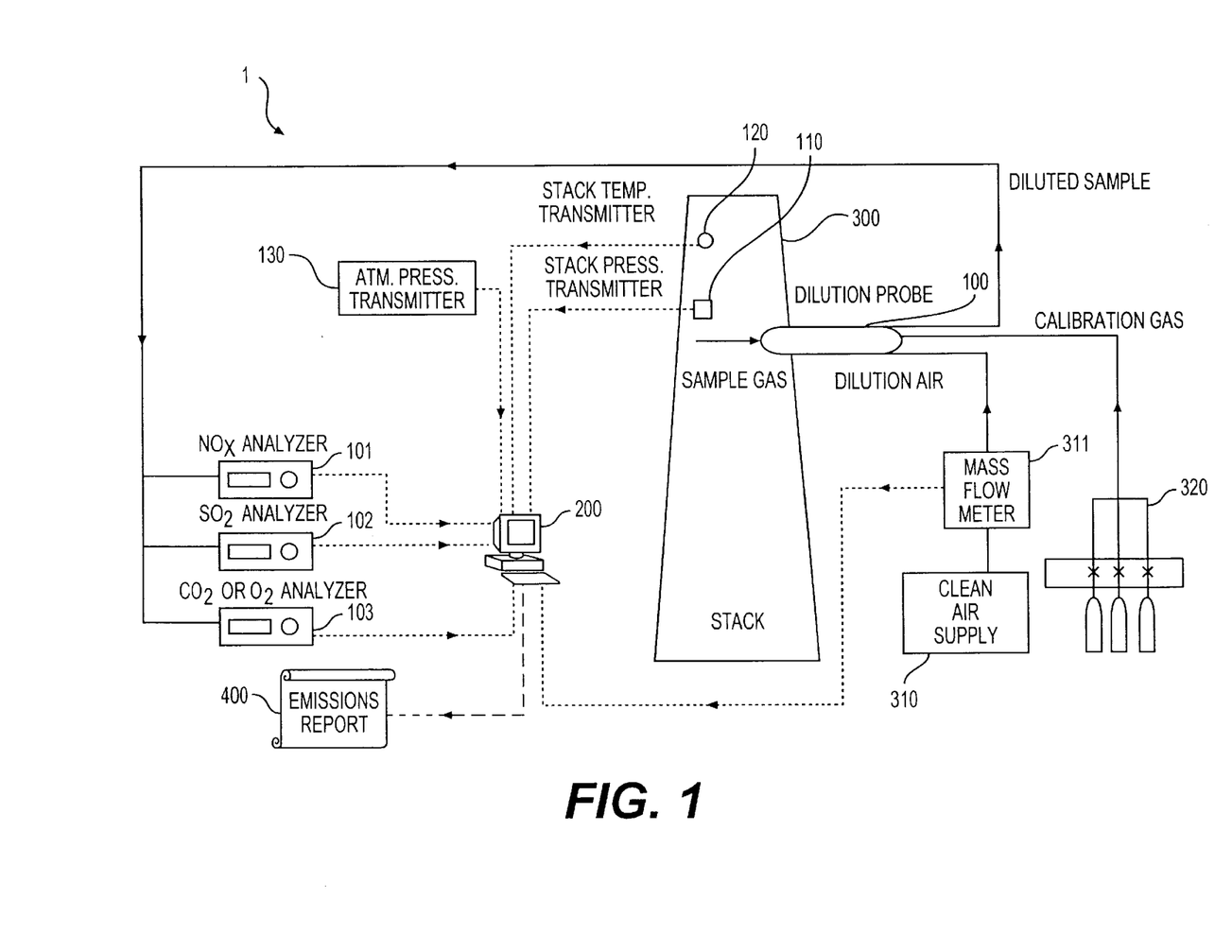
FIG. 1 is a schematic view of an embodiment of the invention.

FIG. 1 shows a schematic view of an embodiment of the invention in which a CEM system 1 includes a dilution probe 100 located in a stack 300. Dilution air is provided to the dilution probe 100 by clean dilution air supply 310. A mass flow meter 311 can be used to measure the amount of dilution air sent to the dilution probe and to report the mass flow of dilution air to a data analyzer 200, e.g. a CPU or a computer. Calibration gas 320 can also be flowed to the dilution probe for calibrating the CEM system 1 at various times.

The dilution probe 100 can be connected via fluid lines, e.g., tubing, to analyzers, such as the $NO_x$ analyzer 101, the $SO_2$ analyzer 102 and the $CO_2$ or $O_2$ analyzer 103. The analyzers communicate to the data analyzer 200 via typical data communication pathways. Alternatively, the analyzers can be incorporated into the data analyzer 200 itself. A stack pressure transmitter 110, a stack temperature transmitter 120, and an atmospheric pressure transmitter 130 can all be connected to communicate variable information to the data analyzer 200. The stack pressure transmitter 110 and stack temperature transmitter 120 are preferably located near the dilution probe to measure the pressure and temperature of the flue gas emitted from the stack near the dilution probe. Alternatively the stack pressure transmitter 110 and stack temperature transmitter 120 are used to measure the respective parameters of the duct or at the sonic orifice stagnation points of the dilution probe 100. The atmospheric pressure transmitter 130 can be located outside of the stack and plant entirely. An emission report 400 can be printed, transmitted or otherwise communicated by the CEM system to provide calculated results from the data analyzer 200.

Figure 2:
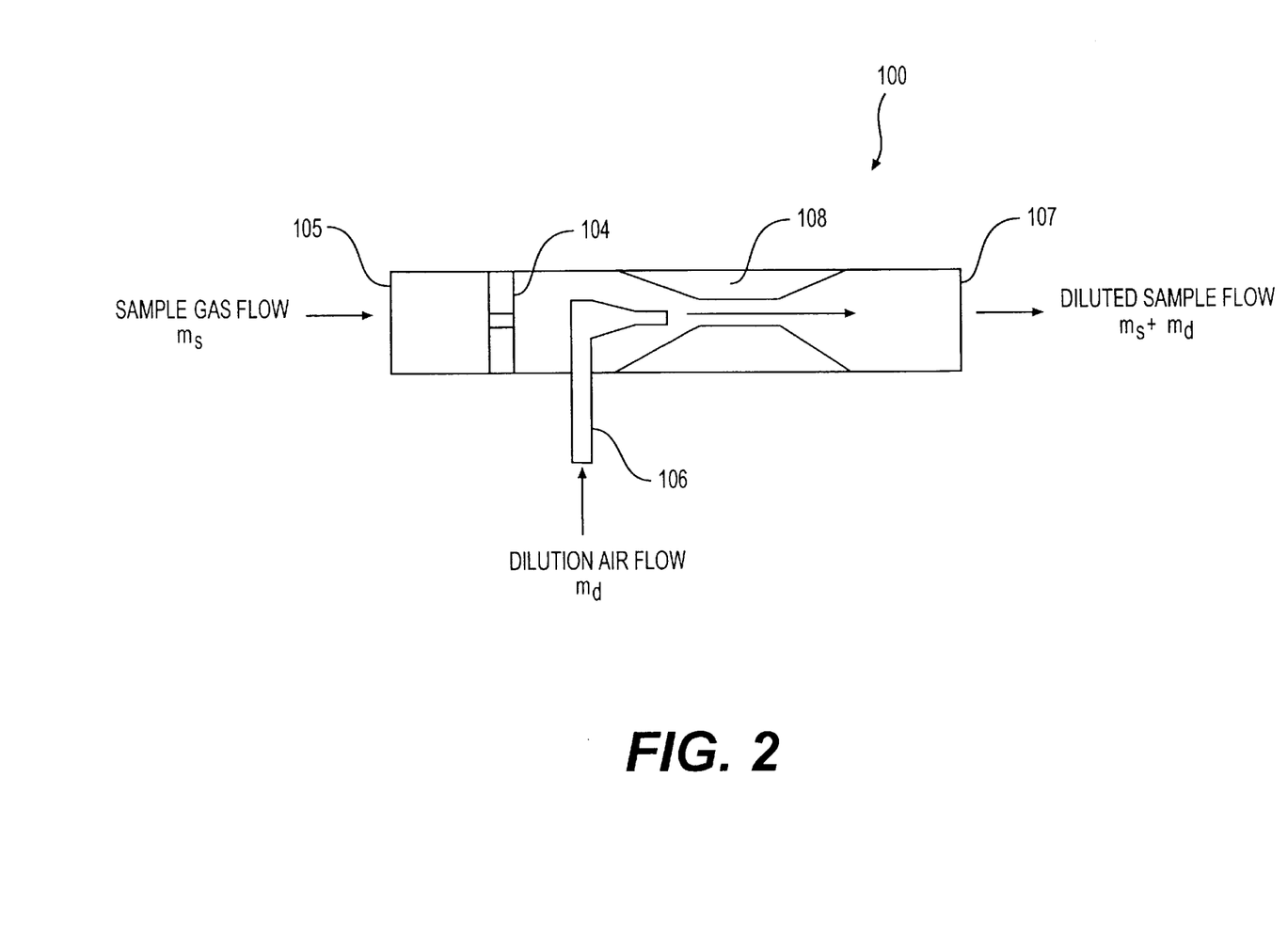
FIG. 2 is a cross-sectional view of a dilution probe venturi of the dilution probe shown in FIG. 1.

FIG. 2 shows a cross section of the dilution probe of FIG. 1. The dilution probe 100 can include a stack or emission source intake 105 that draws a sample mixture of gas and/or materials (flue gas) from an emission source into the dilution probe and through a sonic orifice 104. A dilution air intake 106 is located on the dilution probe and injects dilution gas, for example clean dry air, into the dilution probe. The dilution air can be injected into a venturi nozzle 108 which creates a vacuum and causes the flue gas to be drawn into the dilution probe and through the sonic orifice 104. The dilution air and flue gas mix to form a diluted sample gas, which exits the dilution probe 100 through the diluted sample gas outlet 107.

The dilution probe system dilutes the flue gas flow with dilution air and measures pollutant levels of the resulting diluted sample gas flow. The analyzer reading (expressed as a molar concentration or mole fraction) for the ith pollutant can be written as:

$$C_{analyzer,i} = \frac{n_i}{n_s + n_d} = \frac{\frac{m_i}{M_i}}{\frac{m_s}{M_s} + \frac{m_d}{M_d}} = \frac{\frac{m_i M_s}{M_i m_s}}{1 + \frac{m_d M_s}{M_d m_s}} \quad (4)$$

where n is the molar flow rate of pollutant; m is mass flow rate; and M is molecular weight. The subindexes s and d correspond to flue (stack) gas and dilution air, respectively. The sample or stack concentration of pollutant ith can similarly be expressed as:

$$C_{stack,i} = \frac{n_i}{n_s} = \frac{\frac{m_i}{M_i}}{\frac{m_s}{M_s}} \quad (5)$$

These two equations can be combined to express stack pollutant concentration as a function of the analyzer measured concentration and a dilution ratio defined in terms of mass flow rates and molecular weights as:

$$C_{stack,i} = C_{analyzer,i} \cdot \left[1 + \frac{m_d}{m_s} \cdot \frac{M_s}{M_d}\right] = C_{analyzer,i} \cdot D \quad (6)$$

An intermediate equation derived (extracted) from equation (6) is as follows:

$$D = 1 + [(m_d/m_s)*(M_s/M_d)] \quad (7)$$

Equation (10) below is then substituted in equation (7) above along with the appropriate constants and the molecular weight for air to develop equation (11) below.

When the dilution probe operates in a sampling mode, data obtained from the analyzers 101–103 are typically converted to the source or stack level pollutant concentration by multiplying the analyzer readings by the dilution ratio evaluated at the time of calibration:

$$C_{stack,i} = C_{analyzer,i} \cdot D_o \quad (8)$$

where $C_i$ represents ith pollutant concentration and $D_o$ is the dilution ratio at the time of calibration. The relationship between the actual pollutant concentration at the stack $C_{stack,i}$ and the pollutant level measured at the analyzers $C_{analyzer,i}$ is constant if the dilution ratio does not change over time. In practice, however, the dilution ratio determined at calibration conditions differs from when the system is in sampling mode.

The system and method of the invention compensate for changes in dilution ratio due to variations in operating conditions in the stack and dilution probe system. The approach is based on direct measurement of dilution air flow rate and an algorithm which calculates a corrected dilution ratio based on calculations of the mass flow rate through the sampling orifice (which is based on measurements of actual stack operating conditions and an estimation of the molecular weight of gas passing through the sampling orifice) and the measured dilution air flow rate. Estimation of flue gas molecular weight can be based on the measurement of flue gas $CO_2$ or $O_2$. The approach is also suitable to correct for changes in dilution ratio when the dilution probe is working in calibration mode. In calibration mode, the correction algorithm uses measurements of actual stack operating conditions and the known molecular weight of the calibration gases used for calibrating the dilution probe. The inventive method and apparatus can be used in real-time monitoring applications by, for example, programming the data analyzer 200 (or other data acquisition system) to calculate the dilution ratio as a function of the above measurements and apply the results to determine the stack gas concentrations with greater accuracy and repeatability and over a wider range of operating conditions.

Upon occurrence of a change in dilution probe temperature, umbilical temperature, or dilution air source pressure, the change in dilution air molar (mass) flow rate is sensed and the new value of dilution ratio is calculated. Upon a change in sample gas temperature, absolute pressure, or molecular weight a change in the molar flow rate of sample gas results, and a new value of dilution ratio is calculated via analytical methods. During CEM system calibration or quality assurance testing, molecular weight adjustments to the dilution ratio are applied via analytical methods based on monitoring of the CEM system operating mode. The CEM system's operating mode can be determined by monitoring the calibration gas solenoid valves status, for example FIG. 6, 253, to determine the current mode of operation, e.g., sample, calibration, or error testing mode. The system operating mode determines the corresponding molecular weight that can be used in the real-time calculation of the dilution ratio D using Equation 11.

Molecular weight adjustments during CEM system sample mode operation may be done on a constant basis as set by analysis of historical data, or dynamically by iterative measurement and correction based on the dilution gas content of the sample. An example of a dynamic sample gas molecular weight calculation on a wet basis for combustion processes, when the system is in the sampling mode, is as follows:

$$M_s = 28 + (0.16*\% \ CO_2) + (0.04*\% \ O_2) - (0.10*\% \ H_2O) \quad (9)$$

where % $CO_2$ is the measured carbon dioxide concentration in percent from the CEM $CO_2$ monitoring system output; %

$O_2$ is an estimated concentration in the flue gas expressed in percent; % $H_2O$ is an estimated moisture content of the flue gas expressed in percent; All concentrations are on a wet basis. If additional wet based monitoring systems for $O_2$ and $H_2O$ are available on a basis consistent with the CEM, these measurement values could be substituted for the estimated values described above.

The mass flow rate of sample gas can be calculated using gas dynamic theory of choked flows, as follows:

$$m_s = \alpha C_d \frac{P_{absolute} \sqrt{M} A_o [1 + \beta(T_{stack} - 530)]^2}{\sqrt{T_{stack}}} \quad (10)$$

where $m_s$ is a mass flow rate of the sample gas, $C_d$ is a discharge coefficient based on the nozzle geometry of the critical orifice and must be verified for each application/embodiment (in a particular embodiment, for example, $C_d$=0.95), $\alpha$ is an engineering units conversion factor (preferably, 0.09877), $P_{absolute}$ is the total stack pressure ($P_{stack}+P_{barometric}$) in lb/ft², M is the molecular weight of the sample or calibration gas in lbm/lb-mole, $\beta$ is the thermal expansion coefficient of the orifice material (preferably 1.47*10⁻⁸), $A_o$ is the throat area of the critical orifice in ft², and $T_{stack}$ is the stack temperature in degrees Rankine.

The mass flow rate of dilution air can be directly measured by the dilution air flow meter 311. The dilution ratio can be expressed as follows:

$$D = 1 + \frac{565.338 F_{da} \sqrt{T_{stack}} \sqrt{M} [1 + y(T_{stack} - 530)]}{P_{absolute}[1 + \beta(T_{stack} - 530)]^2} \quad (11)$$

where $F_{da}$ is the mass flow rate of dilution air preferably in standard liters per minute, M is the molecular weight of the sample gas or injected calibration gas in lbm/lb-mole, and y is the gamma constant which is a temperature correction factor for the mass flow measurement and which can be determined experimentally (preferably y=1.9056*10⁻⁴).

Figure 3:
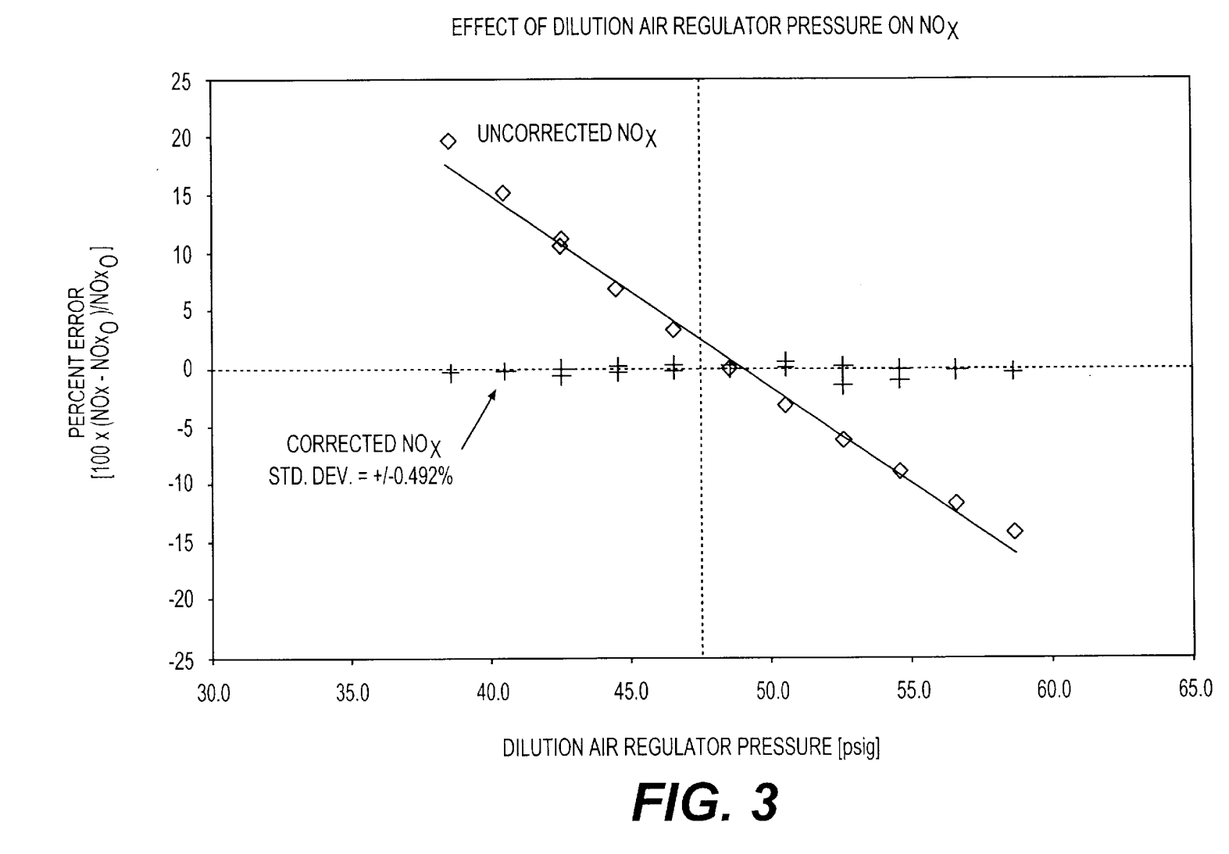
FIG. 3 is a graph of the dilution air regulator pressure vs. the percent error of measurement of $NO_x$.
Figure 4:
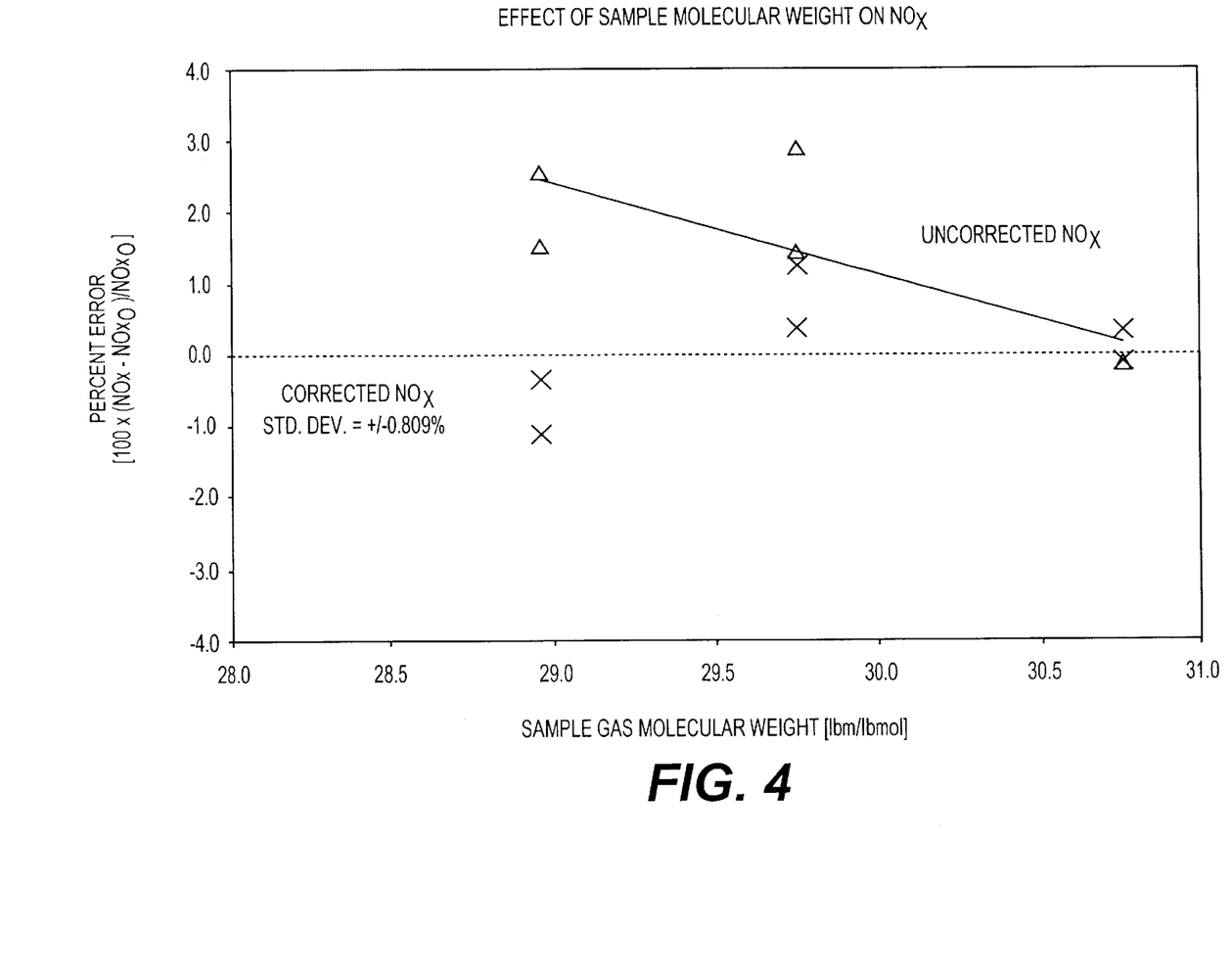
FIG. 4 is a graph of the sample gas molecular weight vs. the percent error of measurement of $NO_x$.
Figure 5:
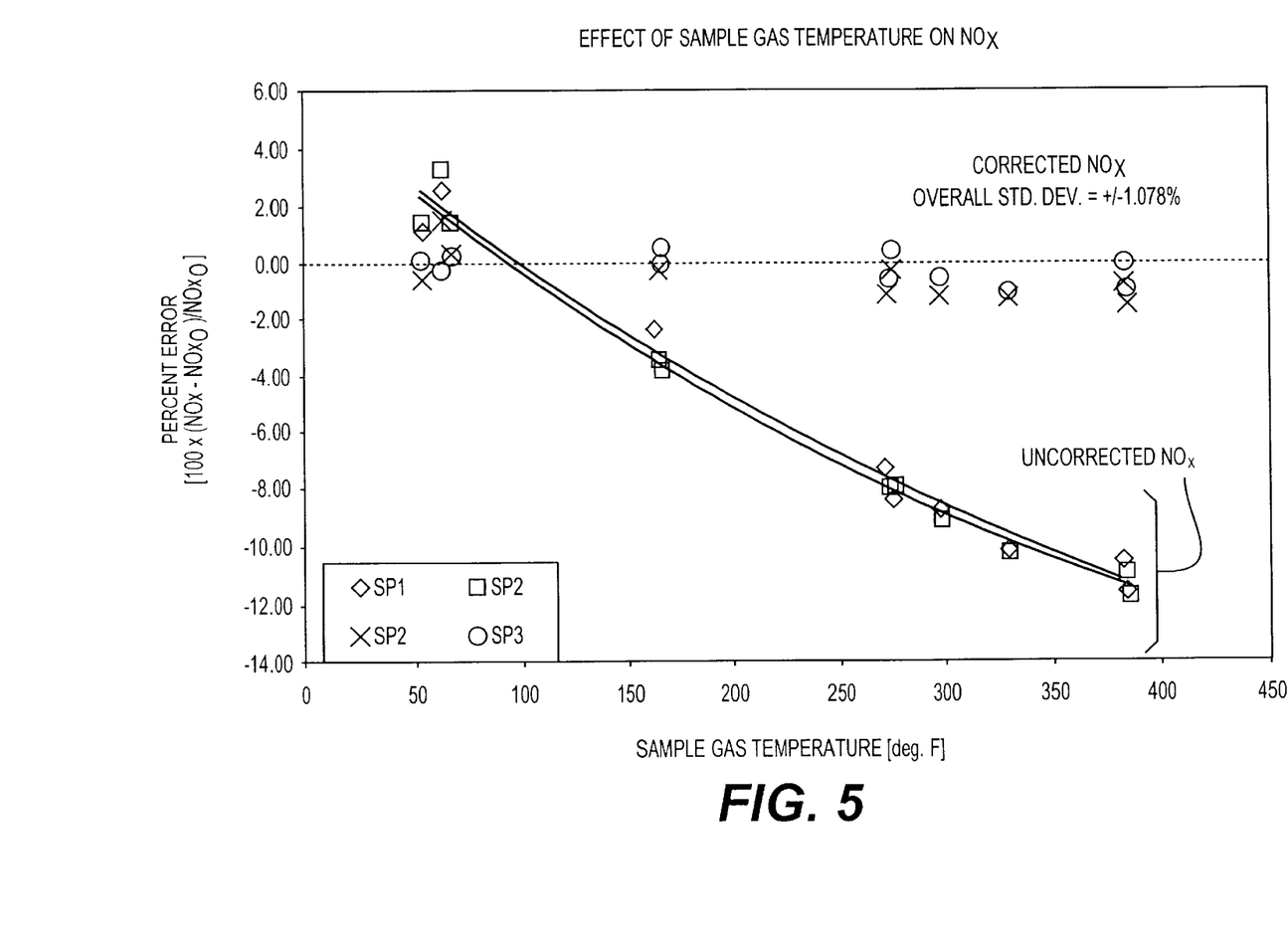
FIG. 5 is a graph of the sample gas temperature vs. the percent error of measurement of $NO_x$.

FIGS. 3–5 show graphs of test results in which laboratory tests were run with a dilution probe 100 using a flow meter 311 to measure the dilution air flow rate and using equation (10) to account for the effects of stack temperature, pressure and flue gas molecular weight on sample gas flow rate. FIG. 3 is a graph that shows the effect of dilution air regulator pressure on the percentage error of $NO_x$ reading. FIG. 4 is a graph that shows the effect of sample gas molecular weight on percentage error of $NO_x$ reading. FIG. 5 is a graph that shows the effect of sample gas temperature on percentage error of $NO_x$ reading. The error in uncorrected $NO_x$ is due to changes in dilution ratio caused by variations in probe operating conditions. The corrected $NO_x$ values were obtained using the system and methods described above and in accordance with the principles of the invention.

The dilution ratio method and apparatus of the invention are based on the physical measurement of dilution air mass flow to the probe and an analytical technique to calculate the mass flow of sampled flue gas. The sampling orifice 104 is a converging duct or nozzle that is typically referred to as a critical or sonic orifice. The mass flow rate of sampled flue gas through the critical orifice is a function of the physical properties of the critical orifice, the molecular weight of the flue gas, and the sampled flue gas pressure and temperature at the inlet to the converging section, i.e., the stagnation pressure and temperature. In the embodiment shown and described with respect to FIG. 1, the stack pressure and temperature are measured and used as the stagnation pressure and temperature input to the algorithm.

Figure 6:
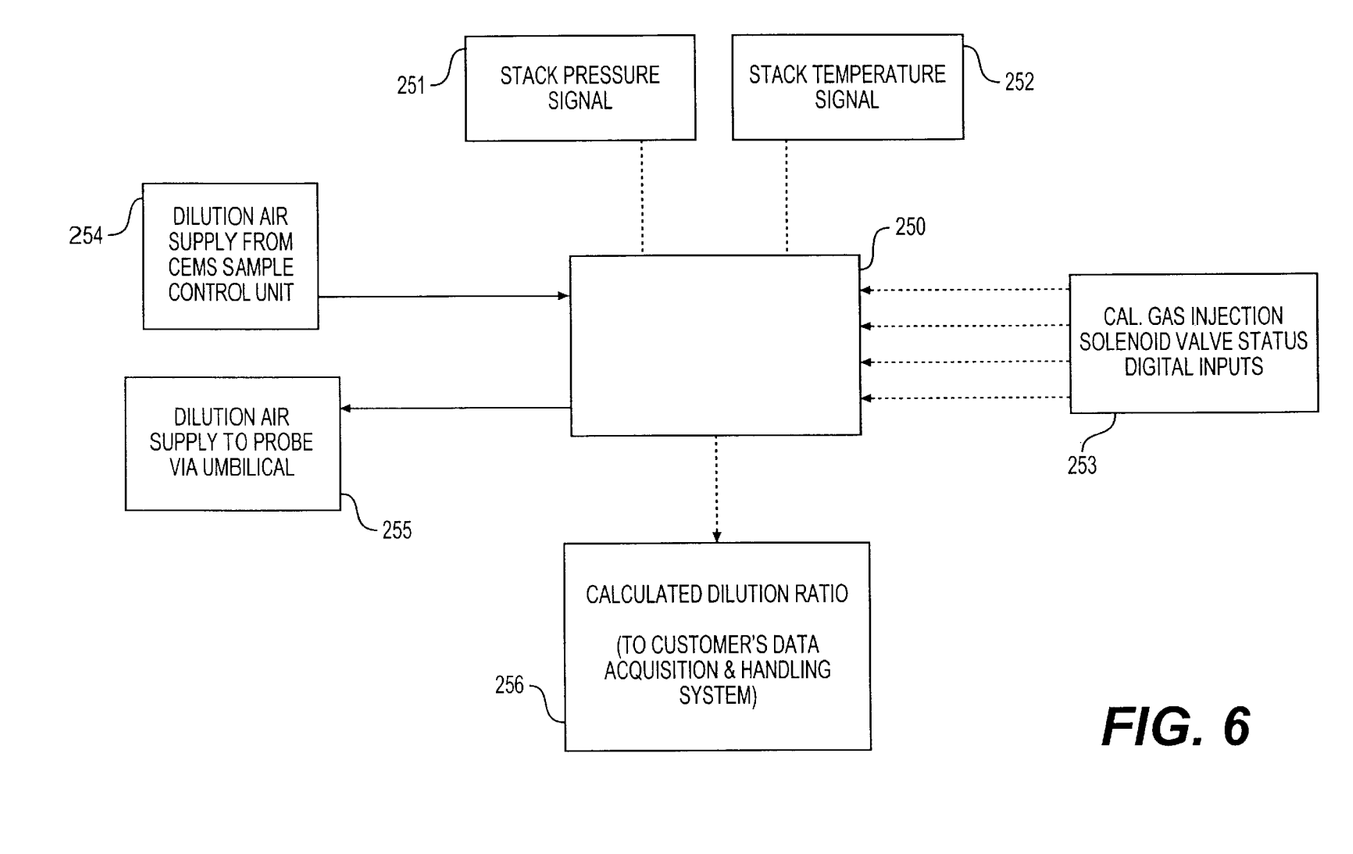
FIG. 6 is a schematic view of another embodiment of the invention designed for use with an existing or independent data acquisition and handling system.

FIG. 6 shows another embodiment of the invention in which the invention is incorporated into a separate, stand-alone CEMS sampling subsystem 250 that is designed for use with an existing Data Acquisition and Handling System (DAHS), e.g., a traditional CEM system, that uses an unheated in-stack dilution probe. The CEMS sampling sub-system 250 can include a data analyzer 251, e.g., laptop computer, stand-alone computer, PLC, or other electronic calculation/data storage and manipulation device. A probe with a critical or sonic orifice that is designed to extract a sample of gas and mix the sample with a dilution gas for analysis at lower concentrations can be included with the sampling sub-system 250. Alternatively, the sub-system could use a critical or sonic orifice dilution probe that is already installed in a particular facility.

The CEMS sampling sub-system 250 provides an electrical signal to the existing DAHS, CEM, or similar system, that is proportional to the dilution ratio. The DAHS, CEM or similar system would then correct the analyzer readings back to stack or duct concentration levels.

The CEMS sampling subsystem 250 shown in FIG. 6 includes a single unheated "EPM" in-stack dilution probe 255 used to extract a flue gas sample. The CEMS sampling subsystem 250 can also include a dilution air mass flowmeter. In operation, the sub-system 250 can calculate the dilution ratio in real time and multiply the dilution ratio by the analyzer-measured pollutant gas concentrations of the diluted sample to continuously compute the concentration of the pollutants in the flue gas.

A maintenance/configuration display can be provided on the CEMS sampling sub-system 250 to monitor, input and change different variables, including measurement, maintenance and test information. Specifically, the following information can be entered through the sub-system 250 display: molecular weights of the flue gas and low, mid and high calibration gases (the calibration gas molecular weights can be calculated via a supplied spreadsheet and must be updated anytime a calibration gas bottle is replaced); a supplied constant derived from the nominal dilution ratio established by the selection of the critical orifice installed in the dilution probe; and other constants as needed for the specific DAHS, CEMS or other system that is being retrofitted with the sub-system 250.

During installation of the sub-system 250, the existing dilution air supply 254 that runs from a sample control unit of an existing CEM system to the probe 255 is routed through the sub-system 250 for monitoring the flow rate of dilution air supplied to the probe 255. The following signals are input to the sub-system 250: a dilution air mass flow rate analog signal; a sampled flue gas pressure analog signal 251 (measured at stack, duct or probe), a sampled flue gas temperature analog signal 252 (measured at stack, duct or probe); possibly a calibration gas mass flow rate signal; possibly a $CO_2$ concentration signal received from existing DAHS or CEMS, etc.; and other digital signals 253 including calibration gas valve status (zero, low, mid and high calibration gas valve status). The sub-system 250 then calculates the dilution ratio based on the calculations and algorithms described above with reference to the embodiment of FIG. 1. An analog dilution ratio signal 256 corresponding to the calculated dilution ratio is preferably output by the sub-system 250 to the existing DAHS, CEM or similar system for correcting the analyzed sample gas measurements to obtain the actual stack emission concentrations.

If a heated in-stack dilution probe is used, a probe heater temperature signal can be fed to the sub-system 250 instead of the stack temperature signal 252. Further, if a heated out-of-stack dilution probe is used, a sampled flue gas pressure signal measured at the probe critical orifice stagnation point is fed to the sub-system 250 instead of the stack pressure signal 251, and a probe heater temperature signal can be fed to the sub-system 250 instead of the stack temperature signal 252.

Retrofitting of facilities that already have a DAHS, CEM or similar system can require some reprogramming of the existing system. Specifically, the existing system may require reprogramming to substitute the use of the CEMS sampling sub-system's dilution ratio signal output 256 in lieu of the existing constant or dilution ratio correction algorithm in the existing DAHS or CEM system.

It should be understood that the above detailed description focuses on particular embodiments of the invention and should not be considered to limit the scope of the invention. Specifically, the invention could be implemented in any type of emission source in which an accurate measure of emission components and/or emitted material is desired. For example, the invention could be implemented in an automobile exhaust, residential chimney or other types of industrial stack without departing from the spirit and scope of the invention. In addition, the dilution probe and analyzers can sample and analyze other materials than those specifically disclosed above. Estimations of variables and/or variable data obtained from other sources can also be used to obtain several of the variable values instead of real time detection and transmission of the data. For example, atmospheric pressure can be estimated by the user prior to using the emission monitoring system. Alternatively, an Internet and/or other data source connection can be provided to the data analyzer 200 to receive atmospheric pressure data and/or other data.

In addition, the dilution probe can be located outside a stack such that it can be easily maintained. In this instance, the dilution probe can be modified to include a pressure sensor to measure the stagnation pressure of emission gas immediately upstream from the probe. The location of the pressure sensor permits an accurate measurement of the stagnation pressure that is realized by the dilution probe.

The location of both the pressure and temperature sensors can also vary provided they give an accurate estimate of the emission source pressure and temperature. The emission source pressure and temperature can be considered the pressure and temperature of an emission gas that was emitted form an emission source, e.g., a stack or duct. The stagnation pressure and temperature can be considered a specific emission source pressure and temperature, respectively.

The application of the invention is not limited to the power generation industry. The inventive system and method can be used in any industry where combustion or similar chemical reaction occurs. Some examples of other facilities that may apply the inventive emission monitoring system and method are co-generation or process steam generators in manufacturing plants of the chemical, oil refining, pulp and paper, and steel industries, as well as other industries.

The invention can also be incorporated into and practiced by a separate data analyzer that is installed into an industrial plant separate from the plant's existing emission monitoring system. The invention would supply the calculated dilution ratio, based on molar flow rates, to the existing emission monitoring system to aid in its calculation of emission constituents. Thus, retrofitting an existing plant with the invention is made easier, more economical and less time consuming.

An alternative approach to calculating the dilution ratio based on the physical measurement of the dilution air mass flow rate is to instead measure the diluted sample mass flow rate. Such a measurement would alter the dilution ratio formula (11), but would be expected to have similar practical results.

Figure 7:
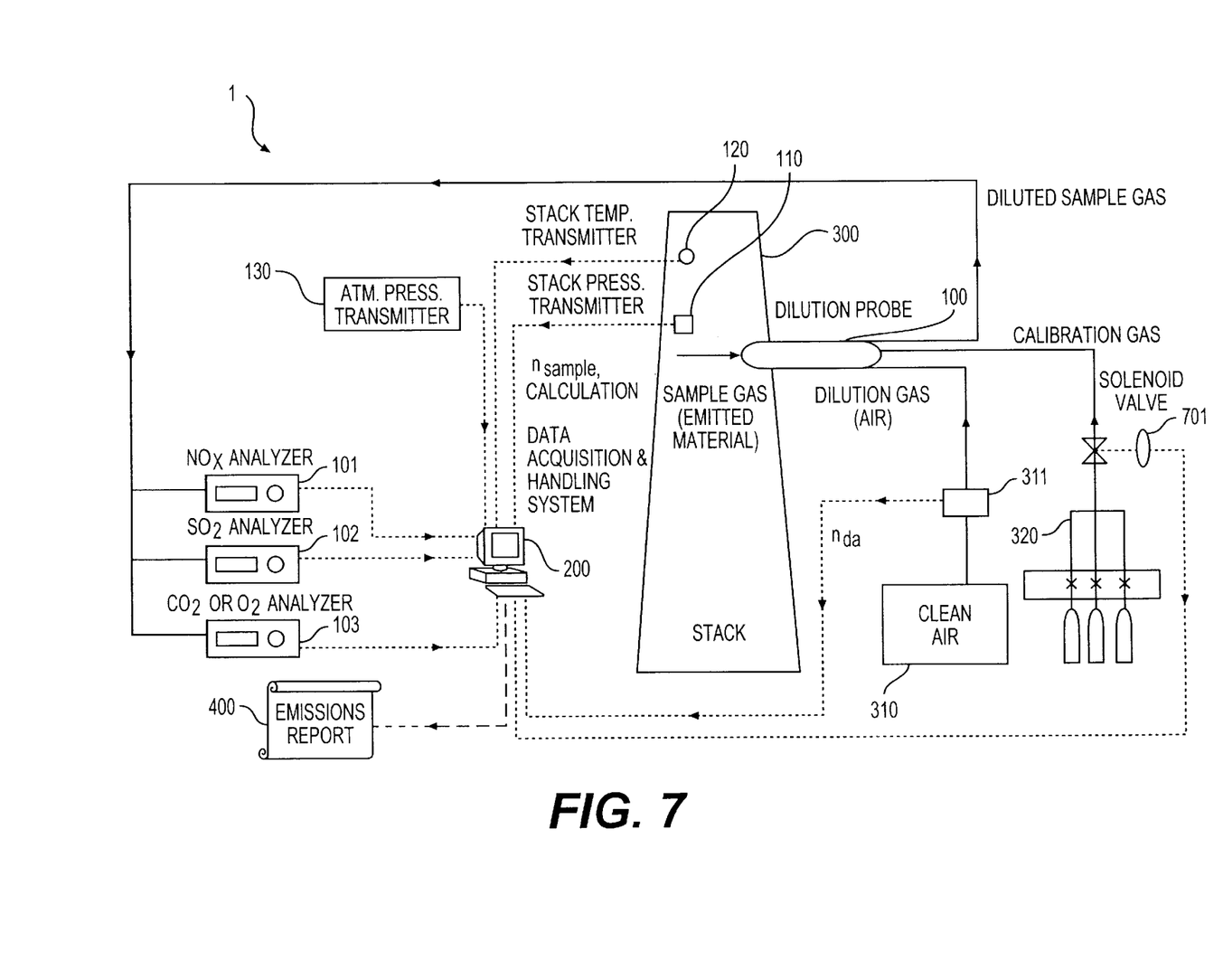
FIG. 7 is a schematic view of another embodiment of the invention designed for use with a new or existing CEM system.

FIG. 7 shows an alternative embodiment of the invention in which a CEM system 1 includes a solenoid valve 701 for selectively directing calibration gas to the data acquisition and handling system 200 for analysis.

It will be apparent to those skilled in the art that various modifications and variations can be made in the method and system of the present invention without departing from the spirit or scope of the invention. Thus, it is intended that the present invention cover the modifications and variations of this invention provided they come within the scope of the appended claims and their equivalents.

What is claimed is:

1. An emission measuring device comprising:
   an analyzer that is capable of measuring a characteristic of an emitted material that is emitted from an emission source,
   means connected to the analyzer for calculating an amount of a particular material contained in the emitted material by using a mass flow rate value, and
   a dilution probe that receives emitted material and dilution gas which forms a mixture known as diluted sample gas, and that is in communication with the analyzer, said mass flow rate value being a value corresponding to one of a mass flow rate of dilution gas, a mass flow rate of sample gas, and a mass flow rate of emitted material.

2. The emission measuring device of claim 1, wherein the dilution probe is located in one of a stack and a duct.

3. An emission measuring device comprising:
   an analyzer that is capable of measuring a characteristic of an emitted material that is emitted from an emission source,
   means connected in the analyzer for calculating an amount of a particular material contained in the emitted material by using a mass flow rate value; and
   a dilution probe connected to said means for calculating and configured to receive a sample gas that includes the emitted material and a dilution gas,
   wherein the means for calculating the amount of a particular material calculates by using a dilution ratio based on the mass flow rate value, and
   wherein the dilution ratio is determined as follows:

$$D = 1 + \frac{565.338 F_{da} \sqrt{T_{stack}} \sqrt{M} [1 + y(T_{stack} - 530)]}{P_{absolute}[1 + \beta(T_{stack} - 530)]^2}$$

where D is the dilution ratio, $F_{da}$ is a mass flow rate of the dilution gas, $T_{stack}$ is an emission source temperature, M is a molecular weight of the emitted material, Y is a constant, $P_{absolute}$ is total emission source pressure, and $\beta$ is a thermal expansion coefficient of orifice material located on the dilution probe.

4. An emission measuring device comprising:
   an analyzer that is capable of measuring a characteristic of an emitted material that is emitted from an emission source; and
   means connected to the analyzer for calculating an amount of a particular material contained in the emitted material by using a mass flow rate value, wherein the means for calculating the amount of a particular material calculates by using a dilution ratio based on the mass flow rate value, and wherein the dilution ration is determined as follows:

$$D=(\dot{n}_{dil}+\dot{n}_{stack})/\dot{n}_{stack}$$

where D is the dilution ratio, $\dot{n}_{dil}$ is a molar flow rate of dilution gas, and $\dot{n}_{stack}$ is a molar flow rate of emitted material.

5. An emission measuring device comprising:
an analyzer that is capable of measuring a characteristic of an emitted material that is emitted from an emission source; and
means connected to the analyzer for calculating an amount of a particular material contained in the emitted material by using a mass flow rate value,
wherein the means for calculating the amount of a particular material calculates by using a dilution ration based on the mass flow rate value, and
wherein the dilution ration is determined as follows:

$$D=1+[(m_d/m_s)*(M_s/M_d)]$$

where D is the dilution ratio, $M_d$ is a mass flow rate of dilution gas, $m_s$ is a mass flow rate of emitted material, $M_d$ is a molecular weight for dilution gas, and $M_s$ is a molecular weight for emitted material.

6. An emission measuring device comprising:
an analyzer that is capable of measuring a characteristic of an emitted material that is emitted from an emission source; and
means connected to the analyzer for calculating an amount of a particular material contained in the emitted material by using a mass flow rate value; and
a dilution probe connected to said means for calculating, wherein the emitted material is combined with a dilution gas to form a sample gas, and the means for calculating the amount of a particular material calculates by using a mass flow rate of sample gas determined as follows:

$$m_s = \alpha C_d \frac{P_{absolute}\sqrt{M}\ A_o[1+\beta(T_{stack}-530)]^2}{\sqrt{T_{stack}}}$$

where $m_s$ is a mass flow rate of the sample gas, is a constant, $C_d$ is a discharge coefficient, $P_{absolute}$ is a total emission source pressure, M is a molecular weight of the sample gas, $\beta$ is a thermal expansion coefficient of an orifice material of the dilution probe, $A_o$ is a throat area of a critical orifice of the dilution probe, and $T_{stack}$ is an emission source temperature.

7. The emission measuring device of claim 6, wherein $T_{stack}$ is the critical orifice upstream staguation temperature.

8. The emission measuring device of claim 6, wherein $P_{absolute}$ is the critical orifice upstream stagnation pressure.

9. An emission measuring device comprising:
an analyzer that is capable of measuring a characteristic of an emitted material that is emitted from an emission source; and
means connected to the analyzer for calculating an amount of a particular material contained in the emitted material by using a mass flow rate value,
wherein the means for calculating includes a data analyzer that is adapted for use with an existing plant data handling and acquisition system.

10. The emission measuring device of claim 9, wherein the data analyzer includes an output line that can be connected to the existing plant data handling and acquisition system to transfer dilution ration data.

11. A system for use with an emission source comprising:
a data medium for receiving emission data collected from one of an analyzer and a transmitter, the emission data including one of a pressure, a temperature, and an amount of a particular material emitted from the emission source;
means for calculating an amount of the particular material emitted from the emission source using a mass flow rate value; and
a dilution probe connected to said means for calculating and configured to receive a sample gas that includes said emitted material and a dilution gas,
wherein the mass flow rate value includes a mass flow rate of a sample gas and said mass flow rate of the sample gas is calculated as follows:

$$m_s = \alpha C_d \frac{P_{absolute}\sqrt{M}\ A_o[1+\beta(T_{stack}-530)]^2}{\sqrt{T_{stack}}}$$

where $m_s$ is a mass flow rate of sample gas, is a constant, $C_d$ is a discharge coefficient, $P_{absolute}$ is total emission source pressure, M is a molecular weight of the sample gas, $\beta$ is a thermal expansion coefficient of an orifice material of the dilution probe, $A_o$ is a throat area of a critical orifice of the dilution probe, and $T_{stack}$ is an emission source temperature.

12. A system for use with an emission source comprising:
a data medium for receiving emission data collected from one of an analyzer and a transmitter, the emission data including one of a pressure, a temperature, and an amount of a particular material emitted from the emission source;
means for calculating an amount of the particular material emitted from the emission source using a mass flow rate value; and
a dilution probe that has an orifice for receiving a sample gas which includes the particular material combined with a dilution gas, wherein the means for calculating an amount of the particular material emitted from the emission source calculates a concentration of the particular material using a dilution ration as follows:

$$D=1+\frac{565.338\ F_{da}\sqrt{T_{stack}}\ \sqrt{M}\ [1+y(T_{stack}-530)]}{P_{absolute}[1+\beta(T_{stack}-530)]^2}$$

where D is the dilution ratio, $F_{da}$ is a mass flow rate of dilution gas, $T_{stack}$ is an emission source temperature, M is a molecular weight of the sample gas, y is a constant, $P_{absolute}$ is total emission source pressure, and $\beta$ is a thermal expansion coefficient of an orifice material of the dilution probe.

13. A system for use with an emission source comprising;
a data medium for receiving emission data collected from one of an analyser and a transmitter, the emission data including one of a pressure, a temperature, and an amount of a particular material emitted from the emission source; and
means for calculating an amount of the particular material emitted from the emission source using a mass flow rate value, where the means for calculating an amount of the particular material emitted from the emission source calculates a concentration of the particular material using a dilution ratio as follows:

$$d=(\dot{n}_{dil}+\dot{n}_{stack})/\dot{n}_{stack}$$

where F is the dilution ration, $\dot{n}_{dil}$ is a molar flow rate of dilution gas, and $\dot{n}_{stack}$ is a molar flow rate of emission gas.

14. A system for use with an emission source comprising:
a data medium for receiving emission data collected from one of an analyzer and a transmitter, the emission data including one of a pressure, a temperature, and an amount of a particular material emitted from the emission source; and
means for calculating an amount of the particular material emitted from the emission source using a mass flow rate value,
wherein the means for calculating an amount of the particular material emitted from the emission source calculates an concentration of the particular material using a dilution ratio; and
a dilution probe connected to an analyzer, the analyzer connected in communication with the means for calculating a total amount of a particular material.

15. A system for use with an emission source comprising:
a data medium for receiving emission data collected from one of an analyzer and a transmitter, the emission data including one of a pressure, a temperature, and an amount of a particular material emitted from the emission source; and
means for calculating an amount of the particular material emitted from the emission source using a mass flow rate value,
wherein the means for calculating includes a data analyzer that is adapted for use with an existing plant data handling and acquisition system.

16. The system for use with an emission source of claim 15, wherein the data analyzer includes an output line that can be connected to an existing plant data handling and acquisition system to transfer dilution ratio data.

17. A method for calculating an amount of a material emitted from a source, comprising the steps of:
sensing an emission gas emitted from the source;
determining a mass flow rate value of the emission gas;
calculating a dilution ration based on the determined mass flow rate value of the emission gas; and
determining a characteristic of the emission gas using the calculated dilution ratio,
wherein the step of sensing includes using a dilution probe configured to receive a sample gas that includes the emission gas and a dilution gas.

18. The method of claim 17, wherein the step of calculating a dilution ratio includes calculating the dilution ration as follows:

$$D = 1 + \frac{565.338\, F_{da}\sqrt{T_{stack}}\,\sqrt{M}\,[1+y(T_{stack}-530)]}{P_{absolute}[1+\beta(T_{stack}-530)]^2}$$

where D is the dilution ratio, $F_{da}$ is a mass flow of dilution gas, $T_{stack}$ is an emission gas temperature, M is the molecular weight of the sample gas, y is a constant, $P_{absolute}$ is total emission source pressure, and $\beta$ is a thermal expansion coefficient of an orifice material of the dilution probe.

19. The method of claim 17, wherein the step of calculating a dilution ratio includes calculating the dilution ratio as follows:

$$D=(\dot{n}_{dil}+\dot{n}_{stack})/\dot{n}_{stack}$$

where D is the dilution ratio, $\dot{n}_{dil}$ is a molar flow rate of dilution gas, and $\dot{n}_{stack}$ is a molar flow rate of emission gas.

20. The method of claim 17, wherein said step of determining a mass flow rate includes determining the mass flow rate as follows:

$$m_s = \alpha C_d \frac{P_{absolute}\sqrt{M}\,A_o[1+\beta(T_{stack}-530)]^2}{\sqrt{T_{stack}}}$$

where $m_c$ is a mass flow rate of emission gas, is a constant, $C_d$ is a discharge coefficient, $P_{absolute}$ is total emission gas pressure, M is a molecular weight of the sample gas, $\beta$ is a thermal expansion coefficient of an orifice material of the dilution probe, $A_o$ is a throat area of a critical orifice of the dilution probe, and $T_{stack}$ is an emission gas temperature.

21. A method for calculating an amount of a material emitted from a source, comprising the steps of:
sensing an emission gas emitted from the source;
determining a mass flow rate value of the emission gas;
calculating a dilution ratio based on the determined mass flow rate value of the emission gas; and
determining a characteristic of the emission gas using th calculated dilution ratio,
wherein the step of calculating includes providing a data analyzer to perform the calculation of the dilution ratio, the data analyzer being capable of retrofitting in an existing data handling and acquisition system at an industrial facility.

22. An emission measuring device comprising:
an analyzer that is capable of measuring a characteristic of an emitted material that is emitted from an emission source; and
a data system connected to the analyzer and configured to calculate an amount of a particular material contained in the emitted material by using a molar flow rate value,
wherein the data system calculates a concentration of the particular material using a dilution ratio, and the dilution ratio is calculated as follows:

$$D=(\dot{n}_{dil}+\dot{n}_{stack})/\dot{n}_{stack}$$

where D is the dilution ratio, $\dot{n}_{dil}$ is a molar flow rate of dilution gas, and $\dot{n}_{stack}$ is a molar flow rate of emission gas.

* * * * *